(12) United States Patent
Abbott et al.

(10) Patent No.: US 8,470,202 B2
(45) Date of Patent: Jun. 25, 2013

(54) METAL PASSIVATION

(75) Inventors: Peter Edward James Abbott, Cleveland (GB); Martin Fowles, North Yorkshire (GB)

(73) Assignee: Johnson Matthey PLC, London (GB)

( * ) Notice: Subject to any disclaimer, the term of this patent is extended or adjusted under 35 U.S.C. 154(b) by 1324 days.

(21) Appl. No.: 12/091,258

(22) PCT Filed: Oct. 10, 2006

(86) PCT No.: PCT/GB2006/050323
§ 371 (c)(1),
(2), (4) Date: Sep. 9, 2008

(87) PCT Pub. No.: WO2007/049069
PCT Pub. Date: May 3, 2007

(65) Prior Publication Data
US 2008/0313962 A1    Dec. 25, 2008

(30) Foreign Application Priority Data
Oct. 24, 2005  (GB) .................................. 0521534.8

(51) Int. Cl.
*C01B 3/26*  (2006.01)
*C23C 22/03*  (2006.01)

(52) U.S. Cl.
USPC .......................................... 252/373; 148/253

(58) Field of Classification Search
USPC ................. 165/134.1; 148/253–256; 252/373
See application file for complete search history.

(56) References Cited

U.S. PATENT DOCUMENTS

| 2,987,427 A | * | 6/1961 | Shaw ............................ 148/253 |
| 3,531,394 A |   | 9/1970 | Koszman |
| 3,785,787 A | * | 1/1974 | Yokota et al. ................. 428/638 |
| 5,856,365 A |   | 1/1999 | Zennaro et al. |
| 5,935,517 A |   | 8/1999 | Röll et al. |

FOREIGN PATENT DOCUMENTS

| EP | 0 724 010 A1 | 7/1996 |
| EP | 1 464 910 A2 | 10/2004 |
| GB | 1 578 270 | 11/1980 |
| RU | 2 161 064 C2 | 12/2000 |
| SU | 480640 | 8/1975 |
| WO | WO-97/05947 A1 | 2/1997 |
| WO | WO-00/09441 A2 | 2/2000 |
| WO | WO-01/66806 A1 | 9/2001 |
| WO | WO-03/051771 A1 | 6/2003 |
| WO | WO 03051771 A1 * | 6/2003 |

* cited by examiner

*Primary Examiner* — Wayne Langel
*Assistant Examiner* — Syed Iqbal
(74) *Attorney, Agent, or Firm* — RatnerPrestia

(57) ABSTRACT

A method for passivating low-alloy steel surfaces in apparatus operating in the temperature range 350 to 580° C. and exposed to a carbon monoxide containing gas mixture comprises adding a passivating compound containing at least one phosphorus (P) atom to the gas mixture. The gas mixture is preferably a reformed gas and also described is a process for producing a synthesis gas wherein, prior to cooling a reformed gas mixture to a temperature between 350 and 580° C. in apparatus having low-alloy steel surfaces downstream of one or more reforming steps, a passivating compound containing at least one phosphorus (P) atom is combined with the gas mixture.

16 Claims, No Drawings

METAL PASSIVATION

CROSS-REFERENCE TO RELATED APPLICATIONS

This application is the U.S. National Phase application of PCT International Application No. PCT/GB2006/050323, filed Oct. 10, 2006, and claims priority of British Patent Application No. 0521534.8, filed Oct. 24, 2005.

FIELD OF THE INVENTION

This invention relates to methods for passivating steel surfaces to prevent undesirable reactions of carbon monoxide with the surfaces at elevated temperatures. In particular this invention is suitable for preventing undesired reactions on low-alloy steel surfaces exposed to synthesis gas streams.

BACKGROUND OF THE INVENTION

Synthesis gas comprising hydrogen and carbon oxides is typically produced by steam reforming and/or partial oxidation of hydrocarbon feedstocks.

WO03/051771 describes a process for preventing unwanted side reactions that occur between carbon monoxide present in a heat exchange medium, including a secondary reformed gas, and the catalytically active metals present on the exterior (shell-side) surface of the steam reformer tubes by adding a passivating compound to the heat exchange medium before it enters the shell side of the heat exchange reformer. The temperature in the shell side of a heat exchange reformer is typically well above 600° C. and this is sufficient to decompose the passivation compound on the metal surface thereby forming stable species on the tube surfaces that are resistant to attack by carbon monoxide. Unlike the downstream apparatus, the internals of the heat exchange reformer apparatus, which are in contact with the reformed gas on the shell-side, are typically fabricated from high temperature resistant low-iron, Ni—Cr alloys and it is believed that the Ni is the source of unwanted side reactions. Whereas phosphorus compounds amongst other compounds are described as suitable passivating compounds for the shell side of the heat exchange reformer there is no suggestion that they may be effective at lower temperatures in low-alloy steel apparatus, such as low-alloy steel apparatus, downstream of the reformer itself. Indeed in WO03/051771 it is suggested that where the passivating species is volatile that absorbent beds be incorporated downstream of the reformer apparatus to recover the passivating species.

In WO 00/09441 a reforming process is disclosed wherein corrosion of the shell side of a heat exchange reformer by a high temperature secondary reformed gas used as heat exchange medium may be reduced by introducing a sulphur compound, such as dimethylsulphide into the secondary reformed gas after it leaves the secondary reforming apparatus and before it enters the heat exchange reformer as heat exchange medium. The amount of sulphur compound necessary to obviate such corrosion problems was stated to be such as to give a sulphur content of 0.2-20 ppm by volume in the secondary reformed gas. Because sulphur only binds weakly to the catalytic metal sites, to prevent contamination and deactivation of catalysts in subsequent process steps, the sulphur compounds were removed by passing the secondary reformed gas exiting the heat exchange reformer through a bed of a suitable absorbent for sulphur compounds, such as zinc oxide. However, the provision of sulphur-removing apparatus adds additional cost and complexity to the reforming process.

WO 01/66806 describes a method for preventing nitridation and/or carburization of metal surface by adding a sulphur compound and a lower amount of a phosphorus compound to the process gas in contact with the metal. It is suggested that the phosphorus compound acts to prevent corrosive sulfidation of the metal surfaces that occurs when sulphur compounds are added to prevent the nitridation and/or carburization reactions. In the examples, addition of 2 ppm of phosphorus in the form of phosphorus pentoxide to a gas containing 20 ppm of hydrogen sulphide completely prevented the sulphur compound from adhering to 12% chromium steel surfaces. However, it was also shown that if the metal surface was subjected to phosphine pre-treatment, nitridation of the metal was not prevented. The requirement for sulphur as well as phosphorus leads to the requirement for expensive sulphur recovery before the syngas may be used in subsequent catalytic processes. Furthermore the unwanted nitridation side reaction was not prevented by the pre-treatment using phosphine indicating that it was ineffective at passivating the metal surface.

We have found a method that overcomes the problems of the above processes.

SUMMARY OF THE INVENTION

Accordingly the invention provides a method for passivating low-alloy steel surfaces in apparatus operating in the temperature range 350 to 580° C. and exposed to a carbon monoxide containing gas mixture comprising adding a passivating compound containing at least one phosphorus (P) atom to said gas mixture.

The invention also provides a method for producing a de-watered synthesis gas comprising the steps of:
(i) subjecting a gaseous mixture containing at least one hydrocarbon to one or more steps of catalytic steam reforming and/or partial oxidation to provide a reformed gas mixture comprising hydrogen, carbon monoxide and steam at a temperature above 580° C.,
(ii) cooling said reformed gas mixture to below the dew point to condense water therefrom, and
(iii) separating said water from said reformed gas mixture to provide a de-watered synthesis gas wherein, prior to cooling said reformed gas mixture to a temperature between 580° C. and 350° C. in apparatus having low-alloy steel surfaces downstream of said one or more reforming steps, a passivating compound containing at least one phosphorus (P) atom is combined with said reformed gas mixture.

DETAILED DESCRIPTION OF THE INVENTION

As mentioned above, synthesis gas is typically produced by steam reforming and/or partial oxidation of hydrocarbon feedstocks. Howsoever the synthesis gas is generated, it comprises varying amounts of hydrogen, steam and carbon oxides. In some processes including a step of steam reforming, it is desirable to operate with as low a steam ratio as possible without forming carbon in the reforming apparatus. However, we have found that where the steam to carbon ratio is low, the carbon monoxide content is sufficiently high to cause reduction of the protective oxide film and subsequent activation of the metal surfaces of downstream equipment. We have found that between 350° C. and 580° C. unwanted side reactions can occur on low-alloy steel surfaces that cause (a) exothermic reactions generating methane and carbon dioxide to take place (b) corrosion of the steel metal surfaces, e.g. by metal dusting and (c) undesirable temperature rises. Loss of metal by corrosion leads to transport of metal atoms downstream, where they can form carbonyl compounds. Volatile metal carbonyls are a health risk and can be potent poisons for downstream catalysts. Downstream equipment such as heat exchangers, boilers and the like are typically fabricated from low-alloy steels. Low-alloy steels become susceptible to activation at different steam to carbon ratios, as the steam addition is reduced.

By "low-alloy steels" we mean alloys of iron with chromium and/or other metals with a total non-iron alloy content of less than 12% by weight. In particular, low-alloy steels are preferably iron alloys with $\leq$10% wt, more preferably $\leq$9% wt total alloy element content. Preferred alloying elements are chromium, molybdenum, vanadium, nickel, niobium and carbon, more preferably chromium or combinations comprising; chromium and molybdenum; chromium, molybdenum and vanadium; carbon and molybdenum; or carbon and nickel. In a particularly preferred embodiment, the low-alloy steel consists of iron, chromium and molybdenum, optionally with minor amounts of other alloying elements.

Chromium is preferably present in the range 0.1 to 10% wt, more preferably 1 to 3% wt. Molybdenum may be present in the range 0.2 to 1.4% wt. Vanadium may be present in an amount in the range 0.04 to 4% wt. Nickel may be present in the range 0.3 to 9.6% wt, preferably 0.3 to 4% wt. Carbon may be present in the range 0.05 to 0.4% wt. Niobium may be present in the range 0.1 to 0.7% wt.

In addition to the above alloying elements, it may be desirable to include micro-alloyed steels that include additions of aluminium and/or titanium in the range 0.01 to 1% wt.

In such alloys, unlike the high chromium alloys having chromium $\geq$12 wt (stainless steels) and nickel alloys used in reformers, the surfaces that form on oxidation of low-alloy steels are primarily iron oxide. Oxidation is primarily by steam present in the synthesis gas and when the steam ratio is too low, the oxide layer does not rapidly re-form at lower temperatures resulting in exposure of the iron surface to carburization. In high chrome alloys, the surfaces that form on oxidation are chromia, which has a different rate of reformation than iron oxide.

The temperature at which the apparatus is operating and therefore of the surfaces exposed to the gas mixture is in the range 350 to 580° C., preferably 350 to 550° C., more preferably 400 to 550° C.

An example of low-alloy steel apparatus is a gas-to-gas heat exchanger. In this equipment, the gas leaving the reformer is cooled such that it is between 350 and 580° C. in part or all of the exchanger. One example of a stream that could be on the opposing side of the heat exchanger is a mixed natural gas and steam stream, being heated prior to passing to the reformer. However, different stream types may be suitable in different processes.

Another example is where the heat given up by the cooling gas is used to generate steam in a boiler. In this case, a significant part of the metal surface separating the cooling gas from the boiling water will be at a temperature close to the water (below 350° C.) and hence not susceptible to corrosion. However, there would be other internal parts of the boiler, which would fall within the temperature range (for example, inlet channel, hot end tubesheet, internal by-pass valve and entrances to tubes).

Another example is where the heat from the cooling gas is used to superheat high pressure steam. In this situation the metal temperatures are likely to be within the temperature range 350-580° C. Historically, there have been a number of instances of superheaters showing susceptibility to metal dusting corrosion.

Yet another example is where the reformed gas is used to heat a liquid. In one embodiment, the liquid could be substantially water, which is heated or heated and partially boiled. The method of the present invention requires the treatment of the surfaces of the apparatus. By treatment we mean coating of the metal surfaces with a passivation compound. Because of the temperatures within the apparatus in use, the passivation compound may undergo some thermal transformation resulting in the formation of passivation species that reduce the interaction between carbon monoxide present in the synthesis gas mixture and the metal surfaces.

The passivation compounds that may be used in the present invention are compounds containing at least one phosphorus (P) atom. Suitable phosphorus-containing compounds include elemental phosphorus (e.g. red P), organic compounds comprising esters of phosphorus oxo-acids, e.g. alkyl- or arylphosphate esters, pyrophosphate esters, phosphite esters, alkyl or arylphosphinic acid esters, alkyl or aryl phosphonic acid esters, phosphine, alkyl or arylphosphines or phosphine oxides and inorganic compounds comprising phosphorus oxides and oxoacids, oxosulphides, phospazines, metal phosphides, and phosphite or phosphate salts. Preferred P-compounds include mono-, di- or tri-esters of phosphorus oxo-acids, particularly phosphate triesters such as trimethyl phosphate, triethyl phosphate and tributyl phosphate; phosphines, especially phosphine $PH_3$ and alkyl or aryl phosphines, such as $PMe_3$, $PEt_3$ or $PPh_3$.

Passivation treatment may be achieved by addition of neat compound or a solution or dispersion of the compound in a suitable diluent to the gas mixture. Alternatively, where the passivation compounds are stable at or above their boiling points, they may be introduced as gases.

The amount of the compound added may be such that phosphorus is present in the gas mixture at a level between 0.01 and 1000 ppm, preferably between 0.05 and 500 ppm by volume, most preferably between 0.1 and 250 ppm by volume and especially between 1 and 100 ppm by volume.

The apparatus may be treated on-line by either a continual or periodic addition of the passivation compound to the gas mixture. Where the treatment is by entrainment in a gas, the passivation compound may be added to the gas at any point before it enters the apparatus, e.g. after a reforming step. Where the treatment is periodic, higher concentrations of phosphorus in the gas, while the treatment is occurring, may be needed than if the treatment is continuous.

Effective treatment of the apparatus according to the method of the present invention results in a reduction of the undesirable carbon monoxide reactions that can occur and a reduction or elimination of an undesirable heat release in the apparatus. The reduction may be observed by monitoring the methane and/or carbon dioxide levels in the gas pre- and post-treatment and/or the temperature of the reformed gas stream leaving the apparatus and/or the temperature of any stream that the reformed gas is being used to heat in the apparatus. The reduction in methane and carbon dioxide or the temperatures that may be achieved depend on the quantity and nature of the passivation compounds as well as the method of treatment of the apparatus and the carbon monoxide content of the gas mixture.

The gas mixture may be any comprising carbon monoxide at high temperature. Preferably the gas mixture is a reformed gas mixture, i.e. a product of steam and/or autothermal reforming and/or partial oxidation of a hydrocarbon feedstock.

Hence the invention further provides a process for producing a de-watered synthesis gas comprising the steps;
(i) subjecting a gaseous mixture containing at least one hydrocarbon to one or more steps of catalytic steam reforming and/or partial oxidation to provide a reformed gas mixture comprising hydrogen, carbon monoxide and steam at a temperature above 580° C.,
(ii) cooling said reformed gas mixture to below the dew point to condense water therefrom, and
(iii) separating said water from said reformed gas mixture to provide a de-watered synthesis gas wherein, prior to cooling said reformed gas mixture to a temperature between 580° C. and 350° C. in apparatus having low-alloy steel surfaces downstream of said one or more reforming steps, a passivating compound containing at least one phosphorus (P) atom is combined with said reformed gas mixture.

The de-watered synthesis gas may be used in processes for the synthesis of methanol, dimethyl ether, ammonia or liquid hydrocarbons by the Fischer-Tropsch process. Such processes are well known. (see for example, *The Catalyst Handbook*, $2^{nd}$ edition, Martyn Twigg ed. Manson Publishing 1996, ISBN 1874545359).

The temperature of the surfaces exposed to the reformed gas mixture is in the range 350 to 580° C., preferably 350 to 550° C., more preferably 400 to 550° C.

In one embodiment, the reforming process to generate the raw reformed gas mixture comprises subjecting a hydrocarbon feedstock/steam mixture to at least one stage (preferably one or two) stages of adiabatic steam reforming, also known as pre-reforming, and then passing the pre-reformed gas fed to an autothermal reformer where it is partially combusted with an oxygen-containing gas and the partially combusted gas passed through a bed of steam reforming catalyst.

In another embodiment of the present invention, the steam reforming is effected using a heat exchange reformer and the process to generate the reformed gas mixture comprises subjecting a mixture of a hydrocarbon feedstock and steam to steam reforming by passing the mixture over a catalyst disposed in externally-heated tubes in a heat exchange reformer to form a primary reformed gas, subjecting the primary reformed gas to secondary reforming by partially combusting the primary reformed gas with an oxygen-containing gas and bringing the resultant partially combusted gas towards equilibrium over a secondary reforming catalyst to form the reformed gas mixture. The heat exchange medium for externally heating the tubes of the heat exchange reformer may be a combusting hydrocarbon fuel, a flue gas or a primary reformed gas that has been subjected to secondary reforming. Preferably the heat exchange medium is the secondary reformed gas mixture, which is used to heat the tubes of the heat exchange reformer, thereby producing a partially cooled reformed gas mixture.

In one type of heat exchange reformer, the catalyst is disposed in tubes extending between a pair of tube sheets through a heat exchange zone. Reactants are fed to a zone above the upper tube sheet and pass through the tubes and into a zone beneath the lower tube sheet. The heating medium is passed through the zone between the two tube sheets. Heat exchange reformers of this type are described in GB 1 578 270 and WO 97/05 947.

In the process, the feedstock may be any gaseous or low boiling hydrocarbon feedstock such as natural gas or naphtha. It is preferably methane or natural gas containing a substantial proportion, e.g. over 90% v/v methane. If the feedstock contains sulphur compounds, before, or preferably after, compression the feedstock is subjected to desulphurisation, e.g. hydrodesulphurization and absorption of hydrogen sulphide using a suitable absorbent, e.g. a zinc oxide bed. The feedstock is typically compressed to a pressure in the range 10-100 bar abs, preferably 20-60 bar abs.

The hydrocarbon may be preheated to a suitable temperature and contacted with water, which is often heated, to generate a steam-hydrocarbon mixture. Steam introduction is preferably effected by saturation of the feedstock by contact of the latter with a stream of heated water in a saturator. The amount of steam generated is preferably such as to give a steam ratio of 0.2 to 1.5, i.e. 0.2 to 2 moles of steam per gram atom of hydrocarbon carbon in the feedstock. The amount of steam is preferably minimised as this leads to a lower cost, more efficient process. It is preferred that the steam ratio is preferably 0.5-1.0.

The hydrocarbon/steam mixture may be subjected to one or more (preferably one or two) stages of pre-reforming. In such a process, the hydrocarbon/steam mixture is heated, typically to a temperature in the range 350-650° C., preferably 400-650° C., and then passed adiabatically through a bed of a suitable catalyst, usually a supported nickel catalyst having a high nickel content, for example above 40% by weight. During such an adiabatic low temperature reforming step any hydrocarbons higher than methane react with steam to give a mixture of methane, carbon oxides and hydrogen. The use of such an adiabatic reforming step, commonly termed pre-reforming, is desirable to ensure that the feed to the heat exchange reformer contains no hydrocarbons higher than methane and also contains a significant amount of hydrogen. This is desirable in order to minimise the risk of carbon formation on the catalyst in the heat-exchange reformer or to suppress soot formation on the autothermal reformer.

If the steam/hydrocarbon or pre-reformed gas mixture is to be primary reformed it is further heated, if necessary, to the heat exchange reformer inlet temperature, which is typically in the range 300-500° C. The mixture is then passed through the catalyst filled tubes of the heat exchange reformer. During passage through the reforming catalyst, the endothermic reforming reaction takes place with the heat required for the reaction being supplied by a combusted fuel gas or preferably from the secondary reformed gas flowing past the exterior surface of the outer tubes. The primary reforming catalyst may be nickel supported on a refractory support such as rings or pellets of calcium aluminate cement, alumina, titania, zirconia and the like. Alternatively a combination of a nickel and precious metal catalyst may be used. For example, a portion of the nickel catalyst may be replaced with a precious metal catalyst, such as a ruthenium-based catalyst.

The temperature of the resulting primary reformed gas is preferably in the range 650-850° C.

The pre-reformed or primary reformed gas may then be subjected to secondary or autothermal reforming. In secondary and autothermal reforming the pre-reformed or primary reformed gas is first subjected to a step of partial combustion in a combustion zone of a secondary or autothermal reformer and the partially combusted gas brought to equilibrium over a fixed bed of steam reforming catalyst disposed underneath the combustion zone. The partially reformed gas from the pre-reformer or primary reformer fed to the combustion zone may additionally comprise a tail gas from a Fischer-Tropsch synthesis and/or, carbon dioxide recovered from the dry synthesis gas. Where primary and secondary reforming are used to produce the reformed gas stream it may also be desirable, in order to reduce the reforming duty on the primary reformer, to bypass a portion of the hydrocarbon (or hydrocarbon/steam mixture) around the primary reformer and feed it directly to the secondary reformer. As an alternative to adding the Fischer-Tropsch tail gas to the partially reformed gas, under low steam ratio conditions it may be desirable where the tail gas contains hydrocarbons other than methane, to feed the tail gas to the hydrocarbon-steam mixture in order to avoid carbon deposition in the secondary reformer.

The combustion stage feed stream comprising the partially reformed gas is then subjected to partial combustion with a gas containing free oxygen supplied via burner apparatus. Whereas some steam may be added to the oxygen containing gas, preferably the amount is minimised, more preferably no additional steam is added so that a low overall steam ratio for the reforming process is achieved. The gas containing free oxygen is preferably substantially pure oxygen, e.g. oxygen containing less than 5% nitrogen. However where the presence of substantial amounts of inerts is permissible, the gas containing free oxygen may be air or enriched air. Where the gas containing free oxygen is substantially pure oxygen, for metallurgical reasons it is preferably fed to the secondary reformer at a temperature below about 250° C.

The amount of oxygen fed to the partial combustion stage may be varied to effect the composition of the reformed gas mixture. Where the partial combustion stage is part of a secondary reforming process and the resulting reformed gas mixture is used to heat the tubes of a heat exchange reformer, the amount of oxygen fed to the partial combustion stage may also be used to control the heat balance of the heat exchange reformer. In general, increasing the amount of oxygen, thereby increasing the temperature of the reformed gas leaving the secondary reformer, causes the $[H_2]/[CO]$ ratio to decrease and the proportion of carbon dioxide to decrease. Alternatively, if the conditions are arranged such that the product composition and temperature is kept constant, increasing the temperature at which the feedstock is fed to the heat exchange reformer decreases the amount of oxygen required (at a constant oxygen feed temperature). Decreasing the required amount of oxygen is advantageous as this means that a smaller, and hence cheaper, air separation plant can be employed to produce the oxygen. The temperature of the feedstock can be increased by any suitable heat source, which may, if necessary, be a fired heater, which of course can use air, rather than oxygen, for the combustion. The amount of oxygen-containing gas added is preferably such that 40 to 70, preferably 40 to 60 moles of oxygen are added per 100 gram atoms of carbon in the hydrocarbon feedstock. The partial combustion reactions may raise the gas temperature of the gas mixture to between 1000 and 1700° C., often to between 1000 and 1500° C.

The hot partially combusted gas then passes though a bed of steam reforming catalyst to form the reformed gas mixture. The steam reforming catalyst is usually nickel supported on a refractory support such as rings or pellets of calcium aluminate cement, alumina, titania, zirconia and the like. The partially combusted gas is cooled as it passed through the bed of steam reforming catalyst. As stated above, the temperature of the reformed gas may be controlled by the amount of oxygen added for the partial combustion step. Preferably the amount of oxygen added is such that the reformed gas mixture leaves the steam reforming catalyst is at a temperature in the range 800-1050° C.

As stated above, the reformed gas mixture may then be used to provide the heat required for a primary reforming step by using the secondary reformed gas as the hot gas flowing in the shell past the tubes of the heat exchange reformer. During this heat exchange, the reformed gas mixture is cooled by transferring heat to the gas undergoing primary reforming. Preferably the secondary reformed gas cools by several hundred degrees centigrade but of course it will leave the heat exchange reformer at a temperature somewhat above the temperature at which the hydrocarbon feedstock/steam mixture is fed to the heat exchange reformer. Preferably the cooled reformed gas mixture leaves the heat exchange reformer shell at a temperature in the range 480-580° C.

In order to remove water from the reformed gas mixture, it is subsequently cooled to below the dew point at which water condenses using one or more heat exchangers. Such cooling may be effected using a stream of cold water and/or by indirect heat exchange. The water condensate is separated from the cooled reformed gas mixture using for example, a separator. Heat recovered during this cooling may be employed for reactants pre-heating and/or for heating water used to provide the steam employed in the steam reforming step. The recovered heat may additionally, or alternatively, be used in a carbon dioxide separation step.

Typically the de-watered synthesis gas contains 5 to 15% by volume of carbon dioxide (on a dry basis). In one embodiment, after separation of the condensed water, carbon dioxide may be separated from the de-watered synthesis gas prior to a Fischer-Tropsch synthesis stage and recycled to the synthesis gas production. Such recycle of carbon dioxide is preferred as it provides a means to control $[H_2]/[CO]$ ratio to achieve the optimal figure for FT synthesis of about 2. Preferably the amount of recycled carbon dioxide is maximised up to the quantity which is needed to achieve this ratio. Where the recycled carbon dioxide (either as carbon dioxide separated from the synthesis gas prior to hydrocarbon synthesis, or as the recycled Fischer-Tropsch tail gas) is added to the partially reformed gas, rather than to the hydrocarbon feedstock prior to steam reforming, there is an advantage in that the steam reforming process can be operated at a lower steam ratio.

Alternatively, or in addition to a stage of carbon dioxide separation and recycle, before the de-watered synthesis gas is passed to a Fischer-Tropsch hydrocarbon synthesis stage it may be subjected to a step of hydrogen separation, e.g. through a membrane, in order to provide pure hydrogen for other uses e.g. hydrocracking or hydrodesulphurization of the hydrocarbon feedstock.

By adding the passivating compound containing at least one phosphorus (P) atom to the reformed gas mixture as described above, corrosion and undesired exothermic side reactions that generate methane and carbon dioxide in the low-allow apparatus are reduced or prevented.

Furthermore by passivating the metal surfaces to reaction with carbon monoxide, the poisoning of downstream catalysts by metal carbonyls should be reduced or eliminated.

EXAMPLES

The invention will be further described by way of the following examples.

Example 1

On a pilot plant a hydrocarbon steam mixture is partially reformed by passing the mixture over a Ni reforming catalyst disposed in an externally heated catalyst tube within a gas heated reformer. The partially reformed gas is passed to a secondary reformer where it is subjected to partial oxidation with oxygen and the resulting partially oxidised mixture brought towards equilibrium over a bed of steam reforming catalyst. The resulting reformed gas stream is then used to externally heat the catalyst-containing reformer tube in the shell of the Gas-Heated Reformer, thereby partially cooling the reformed gas stream. The pipework leaving the Gas- Heated Reformer and the subsequent Gas-to-Gas Heat exchanger downstream are fabricated with Cr—Mo steel internal surfaces (1.25 Cr+0.5 Mo) and are exposed at temperatures in the range 350-510° C.

It was found that at below a steam to carbon ratio of about 1.2 unwanted exothermic reactions between the CO in the reformed gas and the Cr—Mo steel surface took place, resulting in temperature rises in both gas streams leaving the exchanger. In accordance with the prior art it was found that a sulphur compound (dimethyldisulphide, DMDS) had to be injected continuously at an amount of about 10 ppm(vol) S in order to prevent these reactions. Due to the poor bonding of S with the metal, the reactions would recur after about 3 hours if the DMDS addition were stopped. In order to remove sulphur at these levels and protect downstream catalysts from poisoning, S-absorption apparatus would have to be installed.

A mixture of Phosphine ($PH_3$) and $CO_2$ was added to the reformed gas stream at a point between the outlet of the autothermal reformer and the inlet of the shell of the Gas-Heated reformer at a reformed gas temperature of about 1030° C., a pressure of about 25 bar abs. and with operation of the process at a steam to carbon ratio of 1.0. The phosphine containing gas was added at intervals of approximately 48 hours, over a period of approximately 15-20 minutes. During the periods of addition, the injection rate was sufficient to give molar concentrations of 'P' in the gas from 30-130 ppmv. DMDS was also added for the first 10 (ten) days. Upon stopping the DMDS no re-occurrence of the exothermic reactions was observed even after many days. Furthermore, upon reducing the steam to carbon ratio to 0.5, there was no change, despite no further addition of phosphine containing gas to the reformed gas stream.

Example 2

At full-scale production, a Gas Heated Reformer was being used to generate a partially reformed gas, which was then passed to a secondary reformer. The reformed gas leaving the secondary reformer was then cooled in the shell-side of the Gas Heated Reformer, in a process to make synthesis gas for methanol production. Trimethylphosphate was added at intervals of once every 3 days for approximately 15 minutes at a point after the autothermal reformer to give a P content of 15 ppmv in the wet syngas for 8 months. In the process the reformed gas is cooled and the process condensate separated. The resulting de-watered synthesis gas is then passed to a standard copper-zinc alumina methanol synthesis catalyst. No change in the normal deactivation rate of the methanol catalyst was observed. Analysis of the discharged catalyst at shut-down revealed no P on the catalyst. Analysis of the process condensate revealed that at least some of the added P had been removed with the water.

Example 3

In a laboratory reactor, a synthesis gas mixture having the following volumetric composition was passed at 520° C. and 39 bara through a bed of Cr—Mo steel pellets (2.25% Cr and 1.0% Mo) with a Geometric Surface Area of 730 $mm^2$:

| | |
|---|---|
| $H_2$ | 44.7%, |
| CO | 15.1%, |
| $CO_2$ | 5.9%, |
| $H_2O$ | 24.3%, |
| $N_2$ | 10.0%, |
| $CH_4$ | 0.0%. |

The gas flow was 3.15 mols/hr (wet basis).

Water gas shift and methanation reactions occurred. The reaction rates were measured by analysing the gas mixture leaving the reactor. Under steady conditions the following reaction rates were determined:

Water Gas Shift: 0.015 $kgmols/hr/m^2$
Methane formation: 0.0057 $kgmols/hr/m^2$.

Phosphine gas ($PH_3$) was introduced into the nitrogen component of the synthesis gas mixture to give a phosphine level in the reactor of 2 ppmv. Following addition, the reaction rates for Water Gas Shift were reduced by 35%, and those for methane formation by 45%. Increasing the amount of $PH_3$ to 3 ppmv and then 6 ppmv further reduced the water-gas-shift and methanation reactions by 54% and 68% respectively.

Following exposure of the pellets, in the absence of synthesis gas, to $PH_3$ at a level of 20 ppmv in nitrogen at 520° C. for one hour, the reaction rates upon exposure to the above synthesis gas, under the above conditions, for Water Gas Shift were reduced by 71%, those for methane formation by 74%.

The invention claimed is:

1. A method for passivating low-alloy steel surfaces in apparatus comprising exposing said apparatus to a carbon monoxide containing reformed gas mixture at a temperature range 350 to 580° C. and adding a passivating compound containing at least one phosphorus (P) atom to said reformed gas mixture, wherein the low-alloy steel is an iron alloy comprising one or more alloy elements selected from the group consisting of chromium, molybdenum, vanadium, nickel, niobium and carbon, and further wherein the sum of the weight percentages of the one or more alloy elements is ≦12% wt.

2. A method according to claim 1 wherein the low-alloy steel consists of iron and chromium or combinations selected from the group consisting of iron, chromium and molybdenum; iron, chromium, molybdenum and vanadium; iron, carbon and molybdenum; and iron, carbon and nickel.

3. A method according to claim 1 wherein chromium is present in the range 0.1 to 10% wt, molybdenum is present in the range 0.2 to 1.4% wt, vanadium is present in the range 0.04 to 4% wt, nickel is present in the range 0.3 to 9.6% wt, carbon is present in the range 0.05 to 0.4% wt and niobium is present in the range 0.1 to 0.7% wt.

4. A method according to claim 1 wherein the low allow steel includes additions of at least one of aluminium and titanium in the range 0.01 to 1% wt.

5. A method according to claim 1 wherein the low-alloy steel is an iron alloy with ≦10% wt, total alloy element content.

6. A method according to claim 1 wherein the amount of passivating compound added is such that it provides a concentration of phosphorus in the gas mixture between 0.01 and 1000 ppm by volume.

7. A method according to claim 1 wherein the passivating compound is selected from the group consisting of elemental phosphorus, esters of phosphorus oxo-acids, pyrophosphate esters, phosphite esters, alkyl or arylphosphinic acid esters, alkyl or aryl phosphonic acid esters, phosphine, alkyl or arylphosphines, phosphine oxides, phosphorus oxides and phosphorus oxoacids, phosphorus oxosulphides, phospazines, metal phosphides, and phosphite or phosphate salts.

8. A method according to claim 1 wherein the passivating compound is a phosphate triester.

9. A method according to claim 1 wherein the passivating compound is a phosphine.

10. A process for producing a de-watered synthesis gas comprising the steps;
- (i) subjecting a gaseous mixture containing at least one hydrocarbon to one or more steps of catalytic steam reforming and/or partial oxidation to provide a reformed gas mixture comprising hydrogen, carbon monoxide and steam at a temperature above 580° C.,
- (ii) cooling said reformed gas mixture to below the dew point to condense water therefrom, and
- (iii) separating said water from said reformed gas mixture to provide a de-watered synthesis gas wherein, prior to cooling said reformed gas mixture to a temperature between 580° C. and 350° C. in apparatus having low-alloy steel surfaces downstream of said one or more reforming steps, a passivating compound containing at least one phosphorus (P) atom is combined with said reformed gas mixture,
    wherein the low-alloy steel is an iron alloy comprising one or more alloy elements selected from the group consisting of chromium, molybdenum, vanadium, nickel, niobium and carbon, and further wherein the sum of the weight percentages of the one or more alloy elements is $\leq 12\%$ wt.

11. A process according to claim 10 wherein the reforming step (i) comprises one or more stages of adiabatic steam reforming followed by a stage of autothermal reforming.

12. A process according to claim 10 wherein the reforming step (i) comprises a stage of primary steam reforming in a gas-heated reformer followed by secondary reforming in which the primary reformed gas is partially combusted with an oxygen containing gas and the resulting gas mixture brought towards equilibrium over a bed of steam reforming catalyst to produce a secondary reformed gas.

13. A process according to claim 12 wherein the gas heated reformer is heated by the secondary reformed gas.

14. A method according to claim 1, wherein the carbon monoxide containing reformed gas mixture is at a temperature in the range 350-510° C.

15. A method according to claim 1 wherein the apparatus is a heat exchanger.

16. A method according to claim 15 wherein the apparatus is selected from the group consisting of a gas-gas heat exchanger, a heat exchanger used to heat a liquid, a boiler for generating steam, and a heat exchanger for superheating high pressure steam.

\* \* \* \* \*

UNITED STATES PATENT AND TRADEMARK OFFICE
CERTIFICATE OF CORRECTION

PATENT NO.        : 8,470,202 B2                           Page 1 of 1
APPLICATION NO. : 12/091258
DATED             : June 25, 2013
INVENTOR(S)       : Abbott et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1463 days.

Signed and Sealed this
Eighth Day of September, 2015

Michelle K. Lee
*Director of the United States Patent and Trademark Office*